United States Patent [19]

Meyer et al.

[11] Patent Number: 5,106,458
[45] Date of Patent: Apr. 21, 1992

[54] METHOD FOR THE PURIFICATION OF PROPYLENE OXIDE

[75] Inventors: Robert A. Meyer, Ballwin, Mo.; Eileen T. Nguyen, Houston; William A. Smith, Austin, both of Tex.

[73] Assignee: Texaco Chemical Company, White Plains, N.Y.

[21] Appl. No.: 736,365

[22] Filed: Jul. 26, 1991

[51] Int. Cl.$^5$ .................... B01D 3/40; C07D 301/32
[52] U.S. Cl. .......................... 203/38; 203/54; 203/62; 203/81; 203/83; 549/541; 549/542
[58] Field of Search .................. 203/38, 29, 41, 54, 203/62, 81, 83; 549/541, 542

[56] References Cited

U.S. PATENT DOCUMENTS

| | | | |
|---|---|---|---|
| 2,622,060 | 12/1952 | Robeson et al. | 203/53 |
| 2,993,916 | 7/1961 | Normington | 49/542 |
| 3,391,063 | 7/1968 | Sennewald et al. | 549/541 |
| 3,477,919 | 11/1969 | Lichtenwalter et al. | 203/36 |
| 3,629,144 | 12/1971 | Hahn et al. | 549/542 |
| 3,635,803 | 1/1972 | Binns et al. | 204/80 |
| 4,691,035 | 9/1987 | Sanderson et al. | 549/542 |
| 4,772,732 | 9/1988 | Huang et al. | 549/542 |
| 4,831,196 | 5/1989 | Buonicore et al. | 549/542 |
| 4,971,661 | 11/1990 | Meyer et al. | 549/541 |
| 4,977,285 | 12/1990 | Marquis et al. | 549/541 |

FOREIGN PATENT DOCUMENTS 60-199019 10/1985 Japan .................. 549/542

Primary Examiner—Wilbur Bascomb, Jr.
Attorney, Agent, or Firm—Jack H. Park; Kenneth R. Priem; Carl G. Ries

[57] ABSTRACT

Methyl formate is removed from impure propylene oxide by contacting the impure propylene oxide in a treating zone with a basic ion exchange resin for a period of time sufficient to convert the methyl formate to formic acid and methanol, and by withdrawing a substantially methyl formate-free treated propylene oxide product from the treating zone.

10 Claims, 5 Drawing Sheets

METHOD FOR THE PURIFICATION OF PROPYLENE OXIDE

BACKGROUND OF THE INVENTION

1. Field of the Invention

This invention relates to the purification of propylene oxide. More particularly, this invention relates to a process for removing contaminating quantities of methyl formate from impure propylene oxide. Still more particularly, this invention relates to a sequential method for the removal of methyl formate and methanol from propylene oxide.

The epoxidation reaction mixture that is formed when propylene is reacted with tertiary butyl hydroperoxide in solution with tertiary butyl alcohol in the presence of a soluble molybdenum epoxidation catalyst will normally comprise unreacted propylene, propylene oxide, unreacted tertiary butyl hydroperoxide, tertiary butyl alcohol, a soluble molybdenum catalyst and impurities including methyl formate and methanol. The reaction mixture is normally separated by distillation into a plurality of distillation fractions including a recycle propylene fraction, a propylene oxide fraction, a tertiary butyl alcohol fraction, and a heavy liquid distillation fraction containing tertiary butyl alcohol, unreacted tertiary butyl hydroperoxide, heavy impurities and substantially all of the dissolved molybdenum catalyst.

In accordance with the present invention, the impure propylene oxide distillation fraction is brought into contact with a basic ion exchange resin in a treating zone for a period of time sufficient to substantially completely convert the methyl formate to formic acid and methanol. A partially purified substantially methyl formate-free propylene oxide fraction is recovered from the treating zone.

In accordance with a preferred embodiment of the present invention, the partially purified propylene oxide is then charged to an extractive distillation zone where the impure propylene oxide is further purified by extractive distillation with an extractive distillation agent consisting essentially of acetone and water in order to remove methanol.

2. Prior Art

A method for the removal of methanol from propylene oxide by extractive distillation with an aqueous acetone blend is disclosed in Meyer et al. U.S. Pat. No. 4,971,661 which issued Nov. 20, 1990.

It is known to remove methyl formate from propylene oxide by treating the impure propylene oxide with an aqueous base, as shown, for example, by Mitchell et al. U.S. Pat. No. 2,550,847, Lichtenwalter et al. U.S. Pat. No. 3,477,919 and Sanderson et al. U.S. Pat. No. 4,691,035.

It is also known to remove methyl formate from impure propylene oxide by extractive distillation as shown, for example, by Kageyama et al. U.S. Pat. No. 3,838,020.

Robeson et al. U.S. Pat. No. 2,622,060 discloses the removal of methyl formate by extractive distillation employing an aqueous solution of an alkaline compound as the extractant.

Binning et al. U.S. Pat. No. 3,350,417 discloses a method for the production and recovery of propylene oxide by plural stage distillation and caustic addition wherein a methyl formate is removed.

It is known to react a hydroperoxide feedstock such as tertiary butyl hydroperoxide with propylene in solvent solution in the presence of an epoxidation catalyst in order to provide a reaction product comprising unreacted feed components, propylene oxide, t-butyl alcohol, a solvent (which may also be t-butyl alcohol), and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, a tertiary butyl alcohol fraction, etc.

It is also known that methyl formate and methanol are common contaminants for propylene oxide which is removed only with difficulty.

For example, Mitchell et al. U.S. Pat. No. 2,550,847 is directed to a process for separating purified propylene oxide from a crude propylene oxide product contaminated with acetaldehyde, methyl formate, methanol, etc., by treating the crude mixture with an aqueous base followed by recovery of the purified propylene oxide by any suitable means such as by decantation. Mitchell et al. reported a recovery of a product containing 78 to 82 wt. % of propylene oxide which, they stated, could be increased in purity to about 95 to 99% by fractional distillation.

In a process unrelated to the purification of propylene oxide, Goddin et al. in U.S. Pat. No. 2,751,337 disclose a process for separating acetone from a mixture of acetone with methanol and methyl acetate utilizing water as an extractive distillation agent.

Hamlin et al. in U.S. Pat. No. 3,409,513 disclose the hydro-extractive distillation of mixtures comprising acetone, lower aliphatic alcohols and esters of lower aliphatic alcohols with carboxylic acids. It is pointed out by the patentees that acetone, methyl acetate and methanol form an azeotrope boiling at 55.5°–56.5° C. Hamlin et al. propose to recover partially purified acetone from such a ternary azeotrope by liquid-liquid extraction with water followed by hydro-extractive distillation of the aqueous phase in order to obtain a partially purified acetone fraction.

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent.

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 3,881,996 is directed to a distillation sequence employing at least three and optionally four columns for the purification of crude propylene oxide, one of the columns optionally being an extractive distillation column wherein a hydrocarbon such as octane is used as the extractive distillation agent.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

SUMMARY OF THE INVENTION

In accordance with the present invention, an impure propylene oxide fraction, such as an impure propylene oxide distillation fraction, is obtained by the distillation of the reaction mixture formed when propylene is reacted with tertiary butyl hydroperoxide in solution in tertiary butyl alcohol in the presence of a soluble molybdenum catalyst. The impure propylene oxide distillation fraction will typically contain from about 50 to about 5,000 ppm of methyl formate and from about 50 to about 1,000 ppm of methanol. A minor amount of acetone may also be present.

In accordance with the present invention, the impure propylene oxide contaminated with methyl formate is brought into contact with a basic ion exchange resin in a treating zone and contacted therein for a period of time sufficient to substantially completely convert the methyl formate to methanol and formic acid. The formic acid will remain adsorbed on the basic ion exchange resin while the methanol will pass in the treating zone with the impure propylene oxide and any methanol which was initially present in the initial charge.

The properties of basic ion exchange catalysts are shown, for example, in a technical brochure entitled "Ion Exchange Catalysis and Matrix Effects" by Arpitochelli, published by Rohm & Haas in 1980 and by other technical bulletins and brochures published by Rohm & Haas including, for example, a technical bulletin entitled "Rohm & Haas Ion Exchange Resins and Fluid Process Chemicals for Special Applications" published in 1986, a technical bulletin entitled "Amberlite ® IRA-743" and a similar bulletin also directed to Amberlite ® IRA-743 and published by Rohm & Haas.

In accordance with a preferred embodiment of the present invention, the thus partially purified propylene oxide distillation fraction which is substantially free from methyl formate is then charged to an extractive distillation zone where it is subjected to extractive distillation with an extractive distillation agent consisting essentially of acetone and water in order to remove methanol as disclosed in U.S. Pat. No. 4,971,661.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum epoxidation catalyst, a reaction mixture is formed comprising unreacted feed components, propylene oxide, tertiary butyl alcohol and impurities including methyl formate, acetaldehyde, acetone and methanol. A minor amount of water will also frequently be present in the reaction mixture.

It is known to separate the epoxidation reaction product formed by the reaction of propylene with tertiary butyl hydroperoxide in solution with tertiary butyl alcohol in the presence of a soluble molybdenum catalyst to provide a recycle propylene fraction, an impure propylene oxide fraction and a heavier tertiary butyl alcohol fraction.

Although the impure propylene oxide obtained in this fashion will normally be composed of about 95 wt. % or more of propylene oxide, the oxygen-containing impurities such as methyl formate and methanol mentioned above, are removed from the propylene oxide only with difficulty.

Acetone is not very difficult to remove from propylene oxide. Methanol is. The point of U.S. Pat. No. 4,971,661 was to add a common, relatively easily removable contaminant (acetone) to the water extraction distillation agent so that reboiler temperatures would be reduced with a subsequent decrease in propylene glycol, its propylene oxide hydration product.

Methyl formate can be removed from propylene oxide by straightforward distillation with a superfractionator, i.e., a distillation tower with 60+ theoretical trays or by extractive distillation with isooctane. Methyl formate will not be removed from propylene oxide by the extractive distillation agent used in U.S. Pat. No. 4,971,661. This is why, in accordance with the present invention, a basic ion exchange resin bed is incorporated before an extractive distillation tower of the type discussed in U.S. Pat. No. 4,971,661.

It has been discovered in accordance with the present invention that when the impure propylene oxide feedstock is fed to a treating zone containing a basic ion exchange resin and then to an extractive distillation zone, both the methyl formate and the methanol can be removed therefrom without significant loss of propylene oxide when the extractive distillation agent consists essentially of a mixture of an acetone/water blend consisting of 20-30 wt. % acetone.

DESCRIPTION OF THE PREFERRED EMBODIMENT

Figure 1:
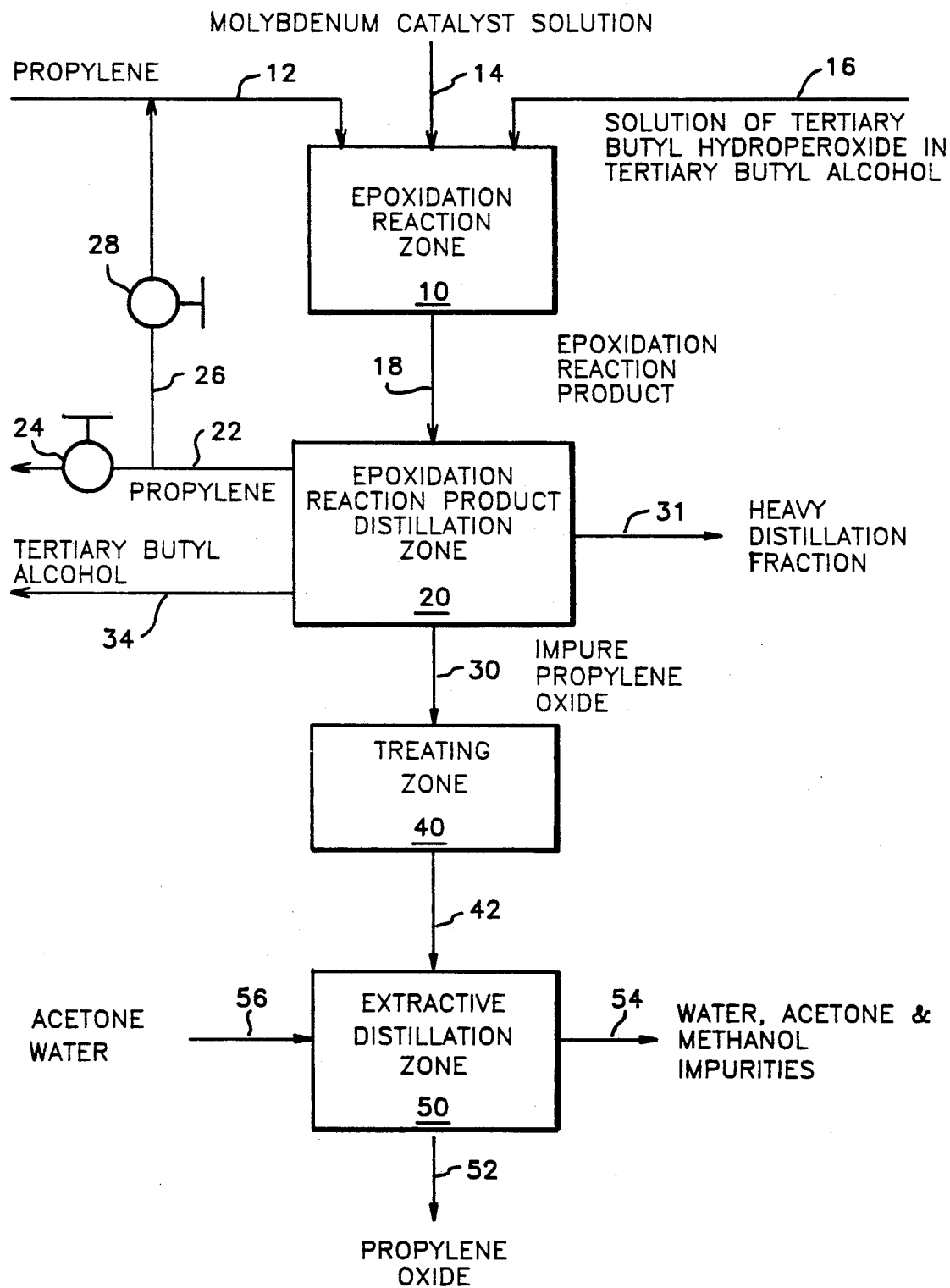
FIG. 1 is a schematic flow chart illustrating the manner in which propylene and tertiary butyl hydroperoxide are reacted in solution in tertiary butyl alcohol in the presence of a molybdenum catalyst to provide an epoxidation reaction product from which a propylene oxide fraction is recovered by distillation and to the purification of the propylene oxide distillation fraction by the removal of methyl formate or both methyl formate and methanol therefrom.

Turning now to FIG. there is shown a schematic flowsheet illustrating a preferred method of practicing the process of the present invention.

An epoxidation reaction zone 10 is provided and propylene is charged thereto by a line 12 together with a soluble molybdenum catalyst charged by a line 14 and a solution of tertiary butyl hydroperoxide and tertiary butyl alcohol is charged by a line 16.

The epoxidation reaction is an epoxidation reaction of the type disclosed by Kollar U.S. Pat. No. 3,351,653 as further elaborated upon, for example, in British patent specification No. 1,298,253 wherein propylene is reacted with tertiary butyl hydroperoxide under reaction conditions including a reaction temperature within the range of about 180° to about 300° F., a pressure of about 300 to about 1000 psig. and, more preferably, a temperature of about 220° F. to about 280° F. and a pressure of about 500 to about 800 psig.

The soluble molybdenum catalyst charged to the epoxidation reaction zone by the line 14 may be an epoxidation catalyst of the type known in the art such as those disclosed by the Kollar patent or the British patent or by Marquis et al. U.S. Pat. No. 4,626,596, U.S. Pat. No. 4,650,886, U.S. Pat. No. 4,654,427, or U.S. Pat. No. 4,758,681. The Marquis et al. patents are directed to molybdenum/alkanol complexes such as solutions of molybdenum compounds in ethylene glycol which contain a high concentration of molybdenum and are particularly useful as catalysts in the epoxidation reaction. Marquis et al. teach, for example, the epoxidation of propylene with tertiary butyl hydroperoxide with their catalyst under epoxidation conditions including a temperature of 50° to 180° C. and a use of propylene to tertiary butyl hydroperoxide molar ratios within the range of about 0.9:1 to about 3.0:1.

Suitably, the tertiary butyl hydroperoxide that is charged to the epoxidation reaction zone 10 by way of line 16 is about a 40 to about 75 wt. % solution of tertiary butyl hydroperoxide in tertiary butyl alcohol. The catalyst is charged to the epoxidation reaction zone 10 by the charge line 14 in an amount such as to provide from about 50 to about 1000 ppm of molybdenum, based on the total of the reactants charged and, more preferably, from about 200 to 600 ppm. The reaction is preferably conducted at superatmospheric pressure such as a pressure of about 300 to 1000 psig.

When the reaction is conducted on a continuous basis, as illustrated in the drawing, the feed materials are charged to the epoxidation reaction zone 10 through the lines 12, 14 and 16 at rates sufficient to maintain the desired concentration of reactants and an equivalent mass of epoxidation reaction mixture is withdrawn from the epoxidation reaction zone 10 by way of a discharge line 18. The reaction product discharged by the line 18 will normally comprise unreacted propylene, a minor amount of unreacted tertiary butyl hydroperoxide, propylene oxide, tertiary butyl alcohol, including tertiary butyl alcohol formed by the reaction of the tertiary butyl hydroperoxide with propylene, the molybdenum catalyst and impurities such as propane, propionaldehyde, acetone, methanol, isopropanol, water, acetaldehyde, methyl formate, acetic acid, formic acid, isobutyric acid, hydrocarbons containing 6 or more carbon atoms, high boiling residue components, etc.

The reaction product 18 is charged to an epoxidation reaction product distillation zone 20 where it is separated by distillation into desired fractions in accordance with methods known to those skilled in the art. For example, the distillation sequence disclosed in British Pat. No. 1,298,253 may be used.

One of the distillate products that is recovered in the zone 20 is a propylene fraction which is discharged by a line 22 controlled by a valve 24 and provided with a branch line 26 controlled by a valve 28 in order to permit the recycle of unreacted propylene to the epoxidation reaction zone 10 through the propylene charge line 12.

Another distillate fraction that is obtained is a propylene oxide product fraction which is discharged by the line 30.

Another product that is recovered from the epoxidation reaction product distillation zone 20 is a tertiary butyl alcohol distillate product discharged through line 40 which may be further purified, if desired, to remove oxygenated impurities therefrom by catalytic treatment as disclosed, for example, in Sanderson et al. U.S. Pat. No. 4,704,482, Sanderson et al. U.S. Pat. No. 4,705,903 or Sanderson et al. U.S. Pat. No. 4,742,149.

A heavy distillation fraction 31, usually a bottoms fraction, is also discharged from the epoxidation reaction product distillation zone 20.

In accordance with the present invention, the impure propylene oxide fraction, which will be contaminated with methyl formate and methanol is charged to a treating zone 40 containing a bed of a basic ion exchange resin such as a styrene-divinyl benzene copolymer containing quaternary ammonium groups such as tetra alkyl ammonium hydroxide groups. Representative products of this nature are sold commercially under trade names such as Dowex ® 1-X10, Dowex ® 2-XB, Amberlite ® IRA-410, Amberlite ® IRA-4015, Amberlite ® IRA-400, Amberlyst ® A-26, Amberlite ® IRA-93, Amberlite ® IRA-94, Amberlite ® IRA-900, Amberlite ® IRA-904, Dowex ® MSA-1, Dowex ® MSA-2, etc.

The impure propylene oxide distillation fraction is treated in treating zone 40 for a period of time sufficient to substantially completely convert the methyl formate to formic acid and methanol. For example, the fraction may be treated at a temperature within the range of about 0° to about 80° C. and passed through the treating zone 40 at a hourly weighted space velocity (WHSV) of about 2 to about 5 lb. of impure propylene oxide per lb. of basic ion exchange resin per hour.

The thus-treated partially purified propylene oxide is discharged from treating zone 40 by a line 42 leading, for example, to an extractive distillation zone 50 constructed and operated as disclosed, for example, in U.S. Pat. No. 4,971,661.

In accordance with this embodiment, an extractive distillation agent consisting of a mixture of acetone and water is charged to the extractive distillation zone 50 by a line 56 and a still further purified propylene oxide distillation product substantially completely free from methyl formate and methanol is discharged by a line 52 while water, acetone, methanol and other by-products are discharged from the extractive distillation zone 50 by a line 54.

Figure 2:
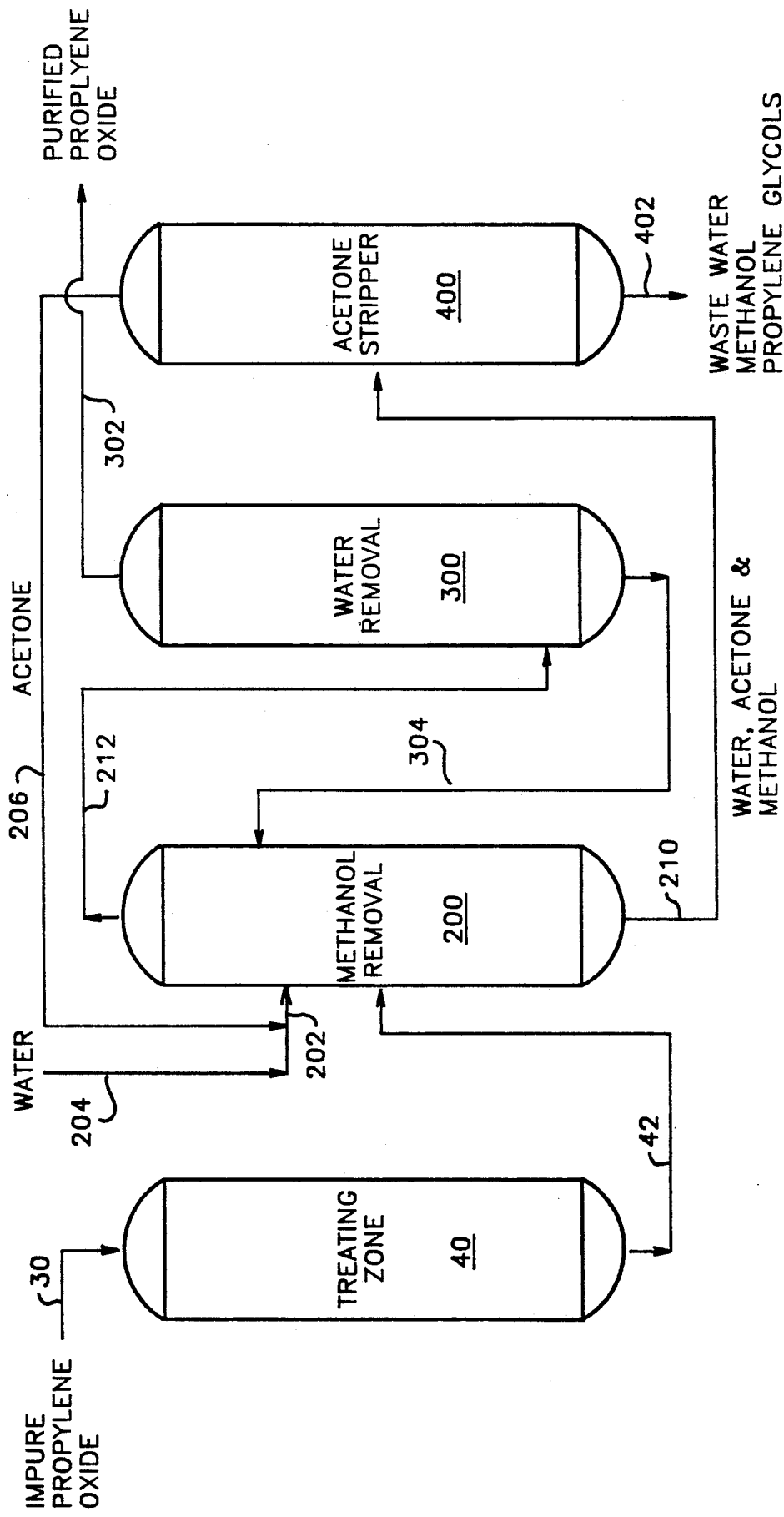
FIG. 2 is a schematic flow sheet with conventional parts omitted showing the general recovery sequence that is used in accordance with the present invention in purifying propylene oxide by the removal of methyl formate and methanol therefrom.

Turning now to FIG. 2, there is shown a schematic flow sheet illustrating a preferred method of practicing the process of the present invention. In the drawing, conventional parts such as valves, pumps, temperature sensors, pressure sensors, heaters, coolers, flow control regulation apparatus, reboilers, reflux condensers, etc., have been omitted.

The impure propylene oxide feedstock that is thus provided from the epoxidation reaction product distillation zone 20 is then purified, which in accordance with the preferred embodiment of the present invention, comprises a treating zone and three distillation columns, each of which is equipped with an appropriate reflux condensing means and an appropriate reboiler heating means.

Thus, in accordance with the present invention, an impure propylene oxide fraction 30 contaminated with impurities including methyl formate, acetaldehyde, acetone, methanol and water is charged to a treating zone 40 which is operated so as to remove methyl formate in the manner described above.

The treating zone 40 contains a bed of a suitable basic ion exchange resin such as Amberlite ® IRA-100 or Amberlite ® IRA-93. For example, the treating conditions established in the treating zone may include, for example, a temperature of about 0° to about 80° C. The propylene oxide may be passed through the bed of ion exchange resin at a weighted hourly space velocity of from about 2 to about 5 lb. of impure propylene oxide distillation fraction 30 per lb. of basic ion exchange bed. As a consequence, substantially all of the methyl formate charged by way of the line 30 is converted to formic acid and methanol. The point of a basic resin is to adsorb an acid from solution. In this case the acid is formic acid. It stays attached to the basic resin matrix until the basic resin matrix is regenerated by a suitable regeneration method of the type known to those skilled in the art.

The effluent from treating zone 40 is charged by line 42 to an extractive distillation column 200 which, in accordance with the present invention, will preferably be a column containing at least about 25 theoretical plates and more preferably, from about 30 to about 50 theoretical plates. The column 200 is suitably operated under distillation conditions including a pressure of about 0 to 30 psig., a reflux ratio of from about 5:1 to about 10:1, a reboiler temperature within the range of about 60° to about 100° C. and a top temperature of about 35° to about 70° C.

The impure propylene oxide is preferably charged to the distillation column 200 in the lower half thereof. An extractive distillation agent composed of an acetone/-water blend consisting of 20-30 wt. % acetone and 80-70 wt. % of water is charged to the upper half of the distillation column 200 by an extractive distillation charge line 202 to which water is charged by a line 204 and to which acetone is charged by a recycle line 206. Reflux is provided by a recycle fraction 304 obtained in a manner to be described.

Within the distillation column 200, substantially all of the methanol, water and acetone introduced into the column 200 by the line 42 and the extractive distillation agent charged by line 202 are removed as a heavier distillation fraction 210 and a partially purified propylene oxide fraction is removed overhead by a line 212, the partially purified propylene oxide fraction containing not more than about 60 ppm of methanol, not more than about 0.02 wt. % of acetone and not more than about 0.3 wt. % of water.

The thus further purified propylene oxide in the line 212 is charged to a third distillation column 300 which is suitably operated under distillation conditions, at about atmospheric pressure including a reflux temperature of about 40° to about 45° C. and a reboiler temperature of about 45° to about 50° C. selected to provide a purified substantially anhydrous propylene oxide distillate fraction which is withdrawn by way of an overhead line 302 and a recycle fraction 304 comprising water and acetone and residual amounts of methanol, if any, which is recycled to the distillation column 200 as reflux as noted above.

The heavier distillation fraction 210 from the column 200 comprising water, methanol and acetone is charged to a fourth distillation column 400 wherein the acetone is separated overhead as a distillate fraction 206 for recycle to the extractive distillation column 200 by way of the extraction agent charge line 202.

A heavier distillation fraction 402 is discharged from the distillation column 400 comprising heavier impurities such as water, methanol, propylene glycols, etc.

The fourth distillation column 400 is operated under distillation conditions including a condenser temperature of about 60° to about 65° C., a reboiler temperature of about 115° to about 125° C. and at about atmospheric pressure.

EXAMPLES

Amberlite ® IRA-900 and Amberlite ® IRA-93 were utilized in a continuous operation resin bed. In continuous operation, a 1" diameter, 5' bed height of resin was used. The feeds contained 500 ppm of methyl formate and 1,000 ppm of water. Results are given in Tables 3, 4 and 5. Plots of breakthrough data are given in FIGS. 3 to 5. The following is apparent:

a. At a WHSV of 2.5 hr$^{-1}$, the methyl formate was reduced to very low levels in the effluent.
b. High recoveries of PO were obtained.
c. Methanol was not observed in the effluent during the early stages of operation because a diffusional steady state for this species had not been reached.
d. Positive breakthrough of methyl formate occurred with these resins after about 24–32 hours of operation at a WHSV of 2.5 hr$^{-1}$.
e. Spent Amberlite ® IRA-93 resin after regeneration with 4% NaOH retained its effectiveness in the removal of methyl formate from propylene oxide.

Figure 3:
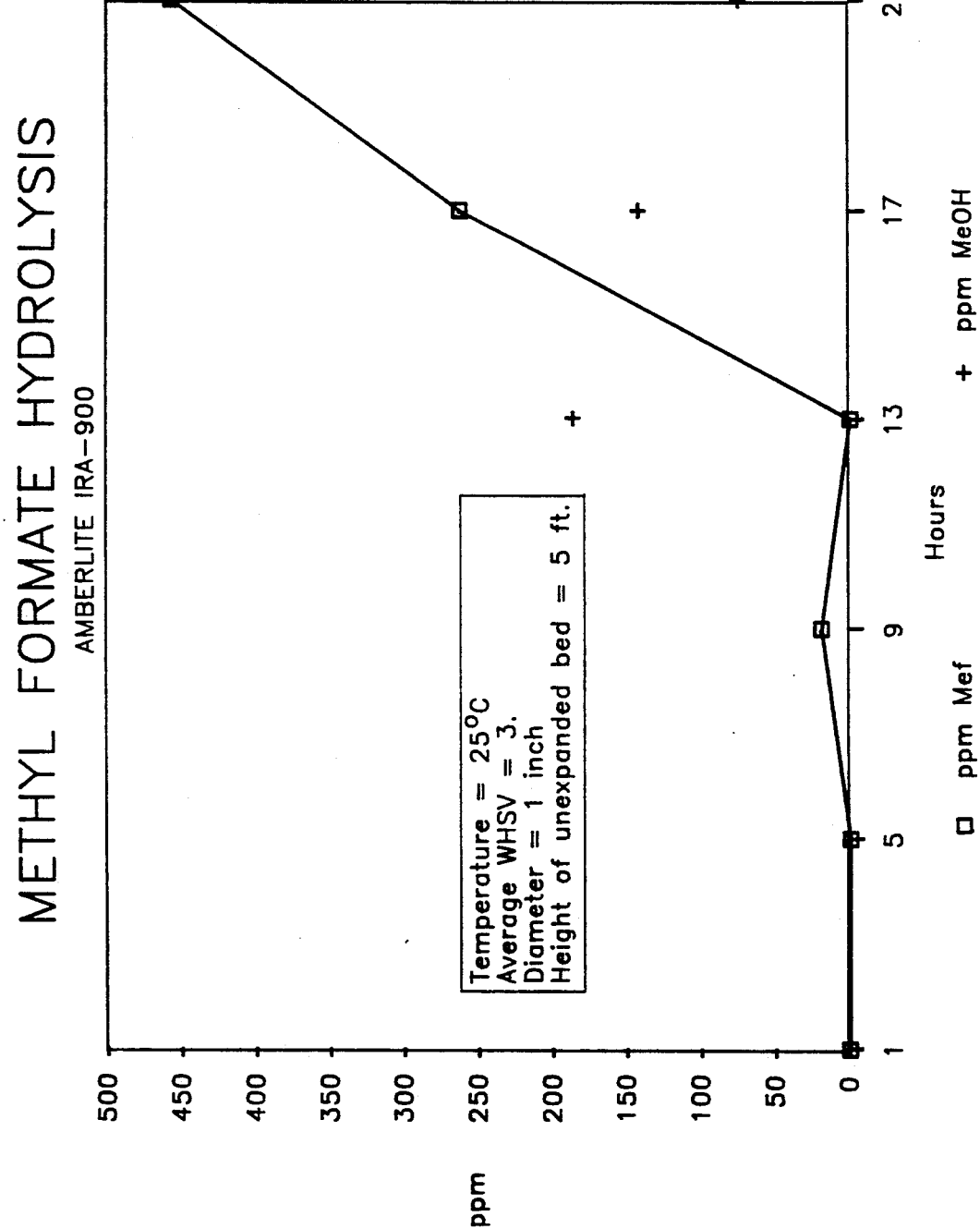
FIGS. 3, 4 and 5 are charts showing the effectiveness of basic ion exchange resins for the removal of methyl formate by treatment with a basic ion exchange resin.

Note from FIG. 3 that when the ion exchange resin was Amberlite ® IRA-900 under the designated treating conditions the effluent was substantially completely free from methyl formate for 13 hours. At the end of that time, the bed began to be saturated with formic acid and the methyl formate broke through.

Figure 4:
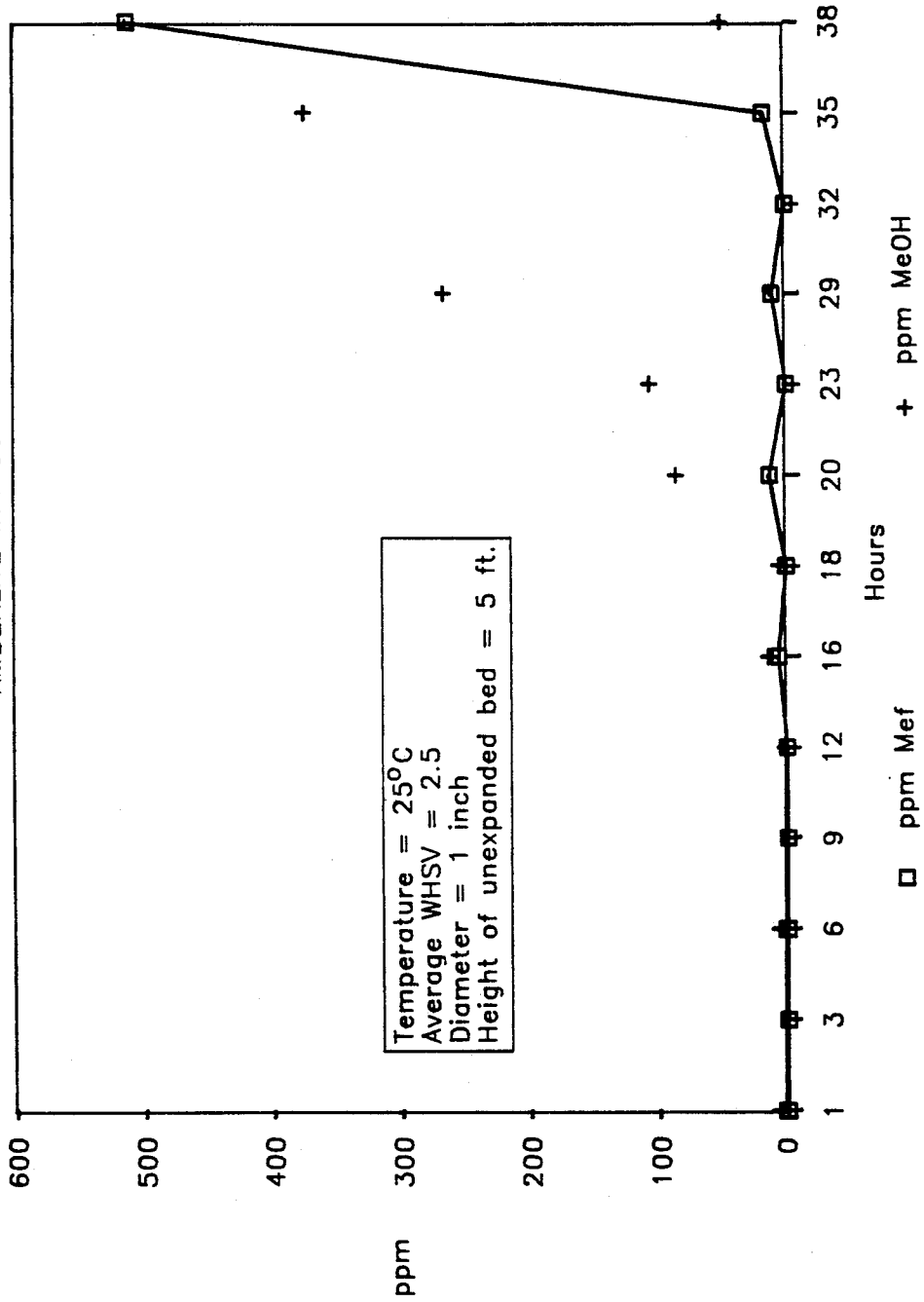

In FIG. 4 it will be noted that under the treating conditions with Amberlite ® IRA-93, an impure propylene oxide feedstock was treated successfully for 35 hours before a breakthrough of the methyl formate occurred.

Figure 5:
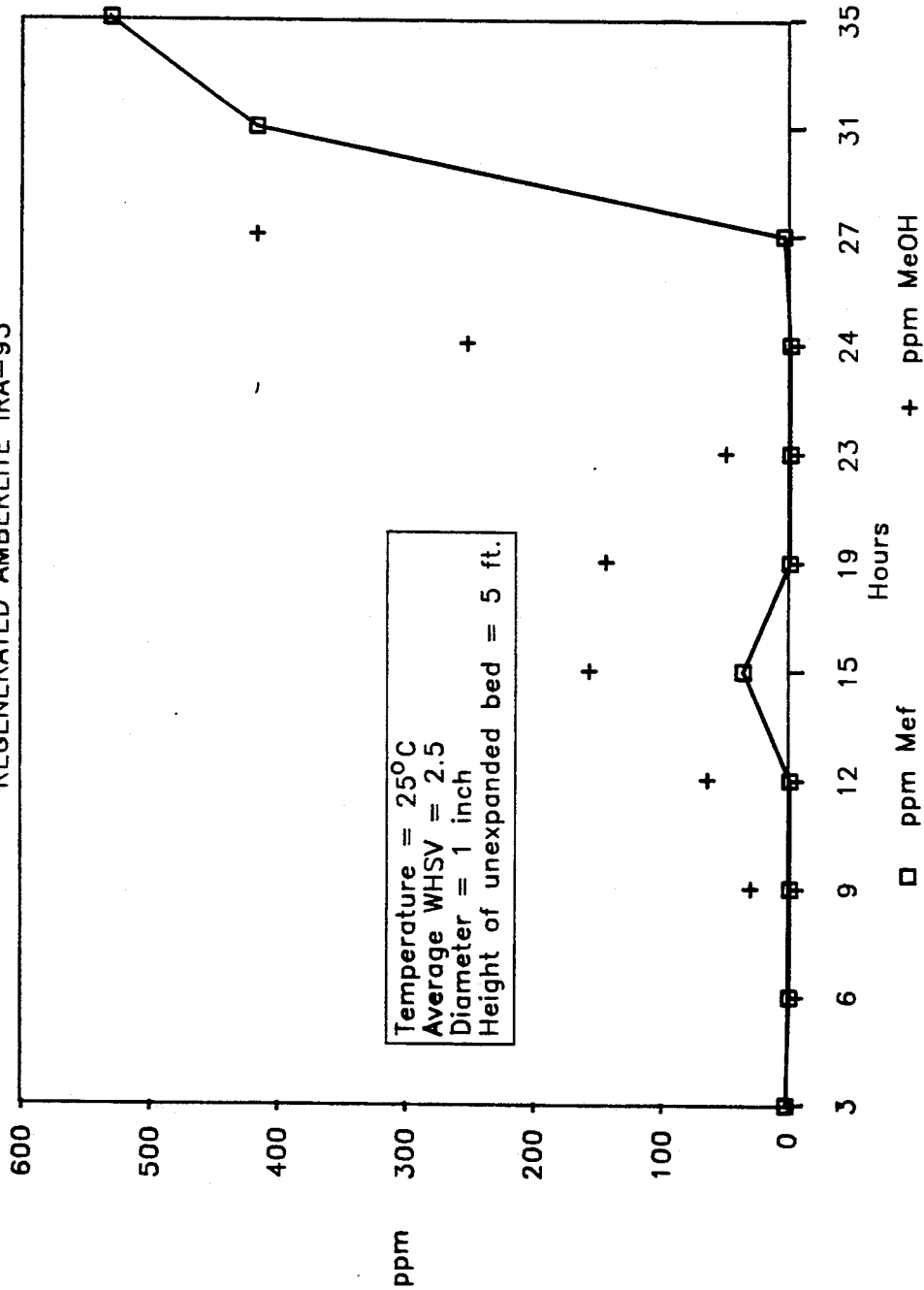

Of particular interest is FIG. 5 which shows the successful results obtained when the Amberlite ® IRA-93 of FIG. 4 was regenerated and again placed on stream. The breakthrough of the regenerated catalyst did not occur until about 27 hours, which is almost the same length of time as for the fresh ion exchange resin.

Shake test results for resins which were screened are given in Tables 1 and 2. The following is apparent:

a. Most resins reduced the methyl formate to very low levels.
b. High recoveries of PO were obtained with most of the resins.
c. There was no advantage in adding excess water to the PO feeds.
d. Since reaction is diffusion limited, reaction rates can be improved by agitation.

For the resin to be successful the following must occur:

a. Reduce methyl formate to low levels.
b. Obtain high recoveries of PO, i.e., the PO composition in the feed and product are nearly identical.
c. Does not discolor the effluent PO.

Based on these results, Amberlite ® IRA-900 and Amberlite ® IRA-93 were chosen for continuous operation.

TABLE 1-A

Screening of Basic Resins for Methyl Formate Hydrolysis at Room Temperature

| | Type (4) | Residence Time Days | Feed Composition PO wt. % | Mef ppm | MeOH ppm | Product Composition PO wt. % | Mef ppm | MeOH ppm | MeOH Bal. wt. % | Notes |
|---|---|---|---|---|---|---|---|---|---|---|
| GEL Type | | | | | | | | | | |
| Dowex 1-X10 | S | 4 | 99.949 | 496.1 | 21.54 | 99.633 | <1 | 237.6 | 83.20 | |
| Dowex 2-X8 | S | 4 | 99.949 | 496.1 | 21.54 | 99.533 | 1.18 | 280.2 | 98.14 | |
| Amberlite IRA-410 | S | 4 | 99.949 | 496.1 | 21.54 | 99.503 | <1 | 307.5 | 107.67 | (3) |
| Amberlite IRA-401S | S | 4 | 99.949 | 496.1 | 21.54 | 98.245 | <1 | | | |
| Amberlite IRA-400 | S | 1 | 99.949 | 496.1 | 21.54 | 92.051 | <1 | 72.07 | 25.24 | (3) |
| MACRORETICULAR TYPE | | | | | | | | | | |
| Amberlyst A-26 | S | 4 | 99.949 | 496.1 | 21.54 | | 463.5 | | | |
| Amberlyst A-21 | W | 4 | 99.949 | 496.1 | 21.54 | | <1 | 11.11 | 3.89 | |
| Amberlite IRA-94 | W | 3 | 99.954 | 403.1 | 25.33 | | <1 | | | |
| Amberlite IRA-94 | W | 1 | 99.954 | 403.1 | 25.33 | 97.488 | 8.406 | 127.8 | 53.30 | |
| Amberlite IRA-93 | W | 3 | 99.954 | 403.1 | 25.33 | | <1 | | | |
| Amberlite IRA-93 | W | 1 | 99.954 | 403.1 | 25.33 | 96.999 | <1 | 153.1 | 63.85 | |
| Amberlite IRA-900 | S | 3 | 99.954 | 403.1 | 25.33 | 99.703 | <1 | 241.8 | 100.84 | |
| Amberlite IRA-900 | S | 1 | 99.954 | 403.1 | 25.33 | | 59.41 | | | |
| Amberlite IRA-904 | S | 3 | 99.954 | 403.1 | 25.33 | 99.802 | <1 | 136.3 | 56.84 | |
| Amberlite IRA-904 | S | 2 | 99.954 | 403.1 | 25.33 | | 1.644 | 136.9 | 57.09 | |
| Amberlite IRA-904 | S | 1 | 99.954 | 403.1 | 25.33 | | 74.43 | | | |
| Dowex MSA-1 | S | 3 | 99.954 | 403.1 | 25.33 | 99.76 | <1 | 251.8 | 105.01 | |
| Dowex MSA-1 | S | 1 | 99.954 | 403.1 | 25.33 | | 33.74 | | | |
| Dowex MSA-2 | S | 3 | 99.954 | 403.1 | 25.33 | 99.671 | <1 | 283.5 | 118.23 | |
| Dowex MSA-2 | S | 1 | 99.954 | 403.1 | 25.33 | | 36.97 | | | |
| Dowex MWA-1 | W | 1 | 99.951 | 374.1 | 25 | 98.16 | <1 | 174.7 | 78.00 | |

Comments:
1. The concentration of water in the feed is 20 wt. %.
2. The PO analyses are based on water-free basis.
3. The PO products are discolored.
4. W = Weakly basic; S = Strongly basic

TABLE 1-B

Screening of Basic Reins for Methyl Formate Hydrolysis at Room Temperature WITH WATER (1)

| | Residence Time Days | Feed Composition PO wt. % (2) | Mef ppm | MeOH ppm | Product Composition PO wt. % (2) | Mef ppm | MeOH ppm | MeOH Bal. wt. % | Notes |
|---|---|---|---|---|---|---|---|---|---|
| GEL TYPE | | | | | | | | | |
| Dowex 1-X10 | 4 | 99.949 | 496.1 | 21.54 | 97.086 | 1.115 | 299.9 | 105.03 | |
| Dowex 1-X8 | 4 | 99.949 | 496.1 | 21.54 | 96.795 | <1 | 178 | 62.33 | |
| Amberlite IRA-410 | 4 | 99.949 | 496.1 | 21.54 | 99.204 | <1 | | | (3) |
| Amberlite IRA-401S | 4 | 99.949 | 496.1 | 21.54 | 90.12 | <1 | | | |
| Amberlite IRA-400 | | | | | | | | | (3) |
| MACRORETICULAR TYPE | | | | | | | | | |
| Amberlyst A-26 | 4 | 99.949 | 496.1 | 21.54 | | 545.3 | | | |
| Amberlyst A-21 | 4 | 99.949 | 496.1 | 21.54 | 74.737 | <1 | <1 | 0.00 | |
| Amberlite IRA-94 | | | | | | | | | |
| Amberlite IRA-94 | | | | | | | | | |
| Amberlite IRA-93 | | | | | | | | | |
| Amberlite IRA-93 | | | | | | | | | |
| Amberlite IRA-900 | | | | | | | | | |
| Amberlite IRA-900 | | | | | | | | | |
| Amberlite IRA-904 | | | | | | | | | |
| Amberlite IRA-904 | | | | | | | | | |
| Amberlite IRA-904 | | | | | | | | | |
| Dowex MSA-1 | | | | | | | | | |
| Dowex MSA-1 | | | | | | | | | |
| Dowex MSA-2 | | | | | | | | | |
| Dowex MSA-2 | | | | | | | | | |
| Dowex MWA-1 | 1 | 99.951 | 374.1 | 25 | 98.245 | <1 | 180.9 | 80.57 | |

Comments:
1. The concentration of water in the feed is 20 wt. %.
2. The PO analyses are based on water-free basis.
3. The PO products are discolored.
4. W = Weakly basic; S = Strongly basic

TABLE 2

Methyl Formate Hydrolysis at Room Temperature and with Stirring

| | Residence Time min. | Feed Composition PO wt. % | Mef ppm | MeOH ppm | Product Composition PO wt. % | Mef ppm | MeOH ppm |
|---|---|---|---|---|---|---|---|
| GEL TYPE | | | | | | | |
| Dowex 2-X8 | 60 | 99.949 | 496.1 | 21.54 | | 183 | |

TABLE 2-continued

Methyl Formate Hydrolysis at Room Temperature and with Stirring

| | Residence Time min. | Feed Composition PO wt. % | Feed Composition Mef ppm | Feed Composition MeOH ppm | Product Composition PO wt. % | Product Composition Mef ppm | Product Composition MeOH ppm |
|---|---|---|---|---|---|---|---|
| | 240 | | | | | 7.75 | |
| MACRORETICULAR TYPE | | | | | | | |
| Dowex MWA-1 | 10 | 99.874 | 503 | 29 | 99.858 | 137.2 | |
| | 20 | | | | 99.266 | 32.26 | |
| | 50 | | | | 99.866 | <1 | |
| Amberlite IRA-93 | 15 | 99.874 | 503 | 29 | | 1 | |
| | 30 | | | | | 36.65 | 309.7 |
| | 45 | | | | | 2.18 | |
| | 60 | | | | 99.871 | <1 | |
| Amberlite IRA-900 | 60 | 99.521 | 374 | 25 | | 1.23 | |
| | 120 | | | | 99.87 | 4.2 | |
| | 180 | | | | | <1 | |

TABLE 3

Breakthrough Data of Methyl Formate Hydrolysis on Amberlite IRA-900
Temperature = 25° C.
Average WHSV = 3.
Diameter = 1 inch
Height of Unexpanded bed = 5 ft

| Feed Concentration | | | | | Effluent Concentration | | | |
|---|---|---|---|---|---|---|---|---|
| wt. % PO by GC | wt. % MF/MeOH by GC | ppm of Mef by IR | ppm of MeOH by IR | Time hrs. | wt. % PO by GC | wt. % MF/MeOH by GC | ppm of Mef by IR | ppm of MeOH by IR |
| 99.944 | 0.054 | 591 | | 1 | | | <1 | |
| | | | | 5 | 99.841 | N/F | <1 | |
| | | | | 9 | 99.752 | 0.018 | 19.68 | |
| | | | | 13 | 99.85 | 0.029 | <1 | 186.8 |
| | | | | 17 | 99.941 | 0.045 | 262.3 | 142.5 |
| | | | | 21 | 99.939 | 0.048 | 457 | |

TABLE 4

Breakthrough Data of Methyl Formate Hydrolysis on Amberlite IRA-93
Temperature = 25° C.
Average WHSV = 2.5
Diameter = 1 inch
Height of Unexpanded bed = 5 ft

| Feed Concentration | | | | | Effluent Concentration | | | |
|---|---|---|---|---|---|---|---|---|
| wt. % PO by GC | wt. % MF/MeOH by GC | ppm of Mef by IR | ppm of MeOH by IR | Time hrs. | wt. % PO by GC | wt. % MF/MeOH by GC | ppm of Mef by IR | ppm of MeOH by IR |
| 99.934 | 0.048 | 453.8 | 47 | 1 | 99.936 | N/F | <1 | 6.5 |
| | | | | 3 | | | <1 | |
| | | | | 6 | 99.674 | N/F | <1 | 6.4 |
| | | | | 9 | 99.558 | N/F | <1 | |
| | | | | 12 | 99.713 | N/F | <1 | 2.3 |
| | | | | 16 | 99.725 | 0.002 | 6.607 | 14.6 |
| 99.949 | 0.044 | 532 | 23.21 | 18 | 99.708 | N/F | <1 | 6 |
| | | | | 20 | 99.877 | 0.01 | 13.23 | 86 |
| | | | | 23 | 99.885 | 0.016 | <1 | 106.2 |
| | | | | 26 | 99.91 | 0.023 | | 220.8 |
| | | | | 29 | 99.901 | 0.03 | 10.85 | 266.2 |
| | | | | 32 | | | <1 | |
| | | | | 35 | 99.921 | 0.044 | 17 | 373.9 |
| | | | | 38 | | | 512 | 50 |

TABLE 5

Breakthrough Data of Methyl Formate Hydrolysis on Regenerated Amberlite IRA-93
Temperature = 25° C.
Average WHSV = 2.5
Diameter = 1 inch
Height of Unexpanded bed = 5 ft

| Feed Concentration | | | | | Effluent Concentration | | | |
|---|---|---|---|---|---|---|---|---|
| wt. % PO by GC | wt. % MF/MeOH by GC | ppm of Mef by IR | ppm of MeOH by IR | Time hrs. | wt. % PO by GC | wt. % MF/MeOH by GC | ppm of Mef by IR | ppm of MeOH by IR |
| 98.488 | 1.498 | 482.9 | 14.9 | 3 | 98.463 | 1.425 | 2.7 | 4.2 |
| | | | | 6 | 98.495 | 1.391 | <1 | |
| | | | | 9 | 98.287 | 1.61 | <1 | 30.9 |
| | | | | 12 | 98.459 | 1.441 | <1 | 65 |
| | | | | 15 | 98.521 | 1.363 | 37 | 157 |
| | | | | 19 | 98.463 | 1.394 | <1 | 144 |

TABLE 5-continued

Breakthrough Data of Methyl Formate Hydrolysis on Regenerated Amberlite IRA-93
Temperature = 25° C.
Average WHSV = 2.5
Diameter = 1 inch
Height of Unexpanded bed = 5 ft

| Feed Concentration | | | | | Effluent Concentration | | | |
| --- | --- | --- | --- | --- | --- | --- | --- | --- |
| wt. % PO by GC | wt. % MF/MeOH by GC | ppm of Mef by IR | ppm of MeOH by IR | Time hrs. | wt. % PO by GC | wt. % MF/MeOH by GC | ppm of Mef by IR | ppm of MeOH by IR |
|  |  |  |  | 23 | 98.605 | 1.374 | <1 | 50.79 |
|  |  |  |  | 24 |  |  | <1 | 252.7 |
| 98.641 | 1.349 | 437.1 | 29.6 | 27 | 98.552 | 1.41 | 5.193 | 415.5 |
|  |  |  |  | 31 |  |  | 417.2 |  |
|  |  |  |  | 35 |  |  | 531.4 |  |

Note: The feeds are contaminated with ethylene oxide. EO shows up in the same peak as MeOH/MF in GC.

What is claimed is:

1. A process for removing methyl formate from impure propylene oxide which comprises the steps of:
    contacting said impure propylene oxide in a treating zone with a basic ion exchange resin for a period of time sufficient to convert said methyl formate to formic acid and methanol, and
    withdrawing a substantially methyl formate-free treated propylene oxide product from said treating zone.

2. A method as in claim 1 wherein the basic ion exchange resin is a styrene-divinyl benzene copolymer containing quaternary ammonium groups.

3. A method as in claim 2 wherein the quaternary ammonium groups are tetralkylammonium hydroxide groups.

4. A method as in claim 1 wherein the impure propylene oxide is brought into contact with the ion exchange resin in the treating zone in liquid phase at a temperature within the range of about 0° to about 80° C.

5. A continuous process for removing methyl formate from impure propylene oxide containing from about 50 to about 5,000 ppm of methyl formate which comprises the steps of:
    continuously flowing said impure propylene oxide through a bed of a basic ion exchange resin in a treating zone under treating conditions including a temperature of about 0° to about 80° C. at a weighted hourly space velocity of about 2 to about 5 lb. of impure propylene oxide per lb. of bed per hour to convert said methyl formate to formic acid and methanol, and
    continuously withdrawing a substantially methyl formate-free treated propylene oxide product from said treating zone.

6. A method as in claim 5 wherein the basic ion exchange resin is a styrene-divinyl benzene copolymer containing quaternary ammonium groups.

7. A method as in claim 6 wherein the quaternary ammonium groups are tetralkylammonium hydroxide groups.

8. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising unreacted propylene, propylene oxide, unreacted tertiary butyl hydroperoxide, tertiary butyl alcohol, dissolved molybdenum catalyst and impurities, including methyl formate and methanol, and wherein the epoxidation reaction product is resolved into distillation fractions in a distillation zone including a distillate propylene fraction, a distillate impure propylene oxide fraction contaminated with methyl formate and methanol, a distillate tertiary butyl alcohol fraction and a heavy liquid distillation fraction composed primarily of tertiary butyl hydroperoxide, tertiary butyl alcohol, the dissolved molybdenum catalyst, and impurities, the improvement which comprises:
    flowing said impure propylene oxide through a bed of a basic ion exchange resin in a treating zone under treating conditions including a temperature of about 0° to about 80° C. at a weighted hourly space velocity of about 2 to about 5 lb. of impure propylene oxide per lb. of bed per hour to convert said methyl formate to formic acid and methanol,
    withdrawing a substantially methyl formate-free partially purified propylene oxide fraction from said treating zone,
    charging said partially purified propylene oxide fraction to the lower half of a distillation column containing a reflux condenser, a reboiler and at least 25 theoretical plates,
    introducing an extractive distillation agent consisting essentially of an acetone/water blend containing about 20 to about 30 wt. % of acetone and, correspondingly, about 80 to 70 wt. % of water at a point 4 to 7 theoretical plates above the partially purified propylene oxide feed point, said extractive distillation agent being introduced into said distillation column in the ratio of said partially purified propylene oxide to said extractive distillation agent of from about 5:1 to about 20:1,
    withdrawing an overhead propylene oxide distillate fraction from said distillation column contaminated with not more than about 60 ppm of methanol, not more than about 0.02 wt. % of acetone and not more than about 0.3 wt. % of water, and
    withdrawing an aqueous bottoms fraction from said distillation column containing substantially all of the methanol, acetone and water introduced into said distillation column.

9. A method as in claim 8 wherein the basic ion exchange resin is a styrene-divinyl benzene copolymer containing quaternary ammonium groups.

10. A method as in claim 9 wherein the quaternary ammonium groups are tetralkylammonium hydroxide groups.

* * * * *